(12) United States Patent
Bell et al.

(10) Patent No.: US 6,210,686 B1
(45) Date of Patent: Apr. 3, 2001

(54) DIETARY SUPPLEMENT AND METHOD FOR LOWERING RISK OF HEART DISEASE

(75) Inventors: Stacey J. Bell, Belmont; R. Armour Forse, Brookline; Bruce R. Bistrian, Ipswich, all of MA (US)

(73) Assignee: Beth Israel Deaconess Medical Center, Boston, MA (US)

( * ) Notice: Subject to any disclaimer, the term of this patent is extended or adjusted under 35 U.S.C. 154(b) by 0 days.

(21) Appl. No.: 09/215,353

(22) Filed: Dec. 18, 1998

(51) Int. Cl.$^7$ .................. A61K 31/355; A61K 31/435; A61K 31/4415; A61K 31/495

(52) U.S. Cl. .................. 424/400; 514/557; 514/568; 514/569; 514/570; 514/576; 514/577; 514/579; 514/613; 514/773; 514/777; 514/778; 514/781; 514/783; 514/786; 514/824; 514/904; 514/948

(58) Field of Search .................. 426/72, 615, 634, 426/648, 656, 658, 808, 810; 424/195.1, 400, 439, 440, 442; 514/183, 247, 248, 249, 252–254, 553, 557, 568, 569, 570, 576, 577, 579, 613, 52, 277, 458, 777, 783, 54, 61, 55, 2, 22, 23, 255.05, 257, 738, 25, 57, 60, 345, 547, 549, 552, 778, 781, 786, 824, 904

(56) References Cited

U.S. PATENT DOCUMENTS

| | | | |
|---|---|---|---|
| 4,810,646 | 3/1989 | Jamas et al. | 435/101 |
| 4,962,094 | 10/1990 | Jamas et al. | 514/54 |
| 5,811,542 | 9/1998 | Jamas et al. | 536/123.12 |
| 5,817,643 | 10/1998 | Jamas et al. | 514/54 |

FOREIGN PATENT DOCUMENTS

| | | | |
|---|---|---|---|
| 0 595 005 | * | 5/1994 | (EP) . |
| WO 97/02356 | | 1/1997 | (WO) . |
| 97/08960 | * | 3/1997 | (WO) . |

OTHER PUBLICATIONS

Braaten, J.T., et al., "Oat Beta–Glucan Reduces Blood Cholesterol Concentration in Hypercholesterolemic Subjects," *Eur. J. Clin. Nutr.* 48:465–474 (1994).

Ripsin, C.M., et al., "Oat Products and Lipid Lowering," *JAMA* 267:3317–3325 (1992).

Davidson, M.H., et al., "Long–term Effects of Consuming Foods Containing Psyllium Seed Husk on Serum Lipids in Subjects with Hypercholesterolemia," *Am. J. Clin. Nutr.* 67:367–376 (1998).

Rimm, E.B., et al., "Folate and Vitamin $B_6$ from Diet and Supplements in Relation to Risk of Coronary Heart Disease Among Women," *JAMA* 279:359–364 (1998).

Malinow, M.R., et al., "Reduction of Plasma Homocysteine Levels by Breakfast Cereal Fortified with Folic Acid in Patients with Coronary Heart Disease," *N. Engl. J. Med.* 338:1009–1015 (1998).

Würsch, P., et al., "The Role of Viscous Soluble Fiber in the Metabolic Control of Diabetes," *Diabetes Care* 20:1774–1780 (1997).

* cited by examiner

*Primary Examiner*—John Pak
*Assistant Examiner*—Frank Choi
(74) *Attorney, Agent, or Firm*—Hamilton, Brook, Smith & Reynolds, P.C.

(57) ABSTRACT

Yeast-derived fiber has been demonstrated, as described herein, to effectively improve the serum lipid profile in humans, when provided as a dietary supplement, without some of the disadvantages known to accompany dietary supplementation with oat fiber or psyllium fiber. Described herein are dietary supplements comprising yeast fiber, e.g., β-glucan or glucomannan, and further comprising folic acid or a salt thereof, vitamin $B_6$, vitamin $B_{12}$, and vitamin E. The dietary supplements of the invention can further comprise fats, carbohydrates and proteins, for example, and other ingredients added to formulate a food product. Such food products can be in the form, for example, of solid or semi-solid foods, such as food bars, pudding, or spreads. By including folate and vitamin $B_6$, the dietary supplement provides a second benefit of suppressing the level of homocysteine in the blood. A third benefit is provided by the anti-oxidant properties of vitamin E, particularly the effect of preserving low density lipoproteins from oxidation. Further embodiments of the invention are methods for improving the serum lipid profile in a human, methods for lowering risk of heart disease, and methods for improving cardiovascular health in a human, comprising administering to the human a dietary supplement of the invention.

17 Claims, 2 Drawing Sheets

DIETARY SUPPLEMENT AND METHOD FOR LOWERING RISK OF HEART DISEASE

BACKGROUND OF THE INVENTION

Ischemic heart disease is a major health problem in the United States. One and half million new cases of heart disease are diagnosed annually; 700,000 of these are diagnosed at the occurrence of an acute myocardial infarction. Nine hundred thousand people die annually of heart disease (http://www.amhrt.org).

The relative risk of mortality from heart disease increases four-fold as the serum cholesterol concentration of the individual goes from 4.32 mmol/L (167 mg/dL) to ≧6.83 mmol/L (264 mg/dL). (Schaefer, E. J., et al., "Individual Variability in Lipoprotein Cholesterol Response to the National Cholesterol Education Program Step 2 Diet," *Am J. Clin. Nutr.* 65:823–830 (1997)). At least 25% of the U.S. population has serum cholesterol levels outside the desirable range. (Sempos, C., et al., "The prevalence of High Blood Cholesterol Levels Among Adults in the United States," *JAAM*, 262:45–52 (1988)). However, a 1% reduction in serum cholesterol concentrations could reduce heart disease by 2%. (Lipid Research Clinics Programs. The Lipid Research Clinics Coronary Primary Prevention Trial Results I: Reduction in Incidence of Coronary Heart Disease, *JAMA*, 251:351–364 (1984); Lipid Research Clinics Programs. The Lipid Research Clinics Coronary Primary Prevention Trial Results II: The Relationship of Reduction in Incidence of Coronary Heart Disease to Cholesterol Lowering, *JAAM*, 251:365–374 (1984).

It is known that changing the fat intake in the diet can significantly alter levels of cholesterol, LDLs and HDLs. The National Cholesterol Education Program (NCEP) limits intakes of total fat (<30% of total energy), saturated fat (<10% of total energy), and cholesterol (<300 mg) (Schaefer, E. J., et al., "Individual Variability in Lipoprotein Cholesterol Response to the National Cholesterol Education Program Step 2 Diet," *Am J. Clin. Nutr.* 65:823–830 (1997)). Patients can expect to experience a reduction in LDL-C (cholesterol in low density lipoproteins, or so-called "bad cholesterol") of 16% to 19%; HDL-C (cholesterol in high density lipoproteins, or so-called "good cholesterol") also declined, 11% for women and 17% for men.

The effects of some different types of soluble fibers on cholesterol levels have been tested. Oat β-glucan can be expected to reduce total serum cholesterol by 2% to 19%. Most studies reported a reduction in LDL-C by 5% to 10%. (Ripsin, C. M. et al., "Oat Products and Lipid Lowering," *JAMA* 267:3317–3325 (1992)). The HDL-C level did not change in this study. The FDA allows a claim to be made on 3 g of oat β-glucan (as three 0.75 g portions) for its cholesterol-lowering effect. Psyllium containing products are also allowed a claim for 1.7 g of soluble fiber portions on four eating occasions for a total of 7 g per day (Davidson, M. H. et al., Long-term Effects of Consuming Foods Containing Psyllium Seed Husk on Serum Lipids in Subjects with Hypercholesterolemia," *Am. J. Clin. Nutr.* 67:367–376 (1998)).

However, food products containing high amounts of fiber from such sources as oats and psyllium suffer from the disadvantage that large amounts must be eaten to achieve the cholesterol-lowering effect, adding unwanted extra caloric intake in the diet. These foods frequently suffer from low palatability and undesirable gastrointestinal effects. A more concentrated and palatable nutritional supplement could provide an alternative to ingestion of oats or psyllium, and to drug therapy for hypercholesterolemia.

SUMMARY OF THE INVENTION

Described herein are dietary supplements that comprise yeast fiber (also "yeast-derived fiber" herein; e.g., β-glucan or glucomannan), and further comprise folic acid or a salt thereof, vitamin $B_6$, vitamin $B_{12}$, and vitamin E. In one embodiment, the yeast fiber is obtained from *Saccharomyces cerevisiae,* but other yeast species can also be sources of the yeast fiber. The dietary supplements of the invention can further comprise fats, carbohydrates and proteins, for example, other vitamins and minerals, and other ingredients, including those added primarily for non-nutritive purposes to formulate a food product, in various amounts and combinations. The nutritional supplement can be formulated as a food to be ingested by itself, as a food additive to be added to or combined with another food or as a nutritional supplement in the form of a tablet or capsule. In a preferred embodiment, the dietary supplement can be provided as a beverage, a solid or semi-solid, and most preferably as an extruded bar.

One embodiment of the invention is a dietary supplement which supplies, in a recommended daily intake of the dietary supplement, nutrients comprising from about 1 gram to about 50 grams yeast-derived fiber, from about 1 μg to about 1,000 μg folic acid, from about 1 mg to about 100 mg vitamin $B_6$, from about 1 μg to about 2,000 μg vitamin $B_{12}$, and from about 10 I.U. to about 800 I.U. vitamin E. A preferred embodiment of the invention is a dietary supplement which supplies, in a recommended daily intake of the dietary supplement, nutrients comprising from about 5 grams to about 20 grams yeast-derived fiber, from about 180 μg to about 800 μg folic acid, from about 1.6 mg to about 4.6 mg vitamin $B_6$, from about 1.5 μg to about 4.0 μg vitamin $B_{12}$, and from about 135 I.U. to about 150 I.U. vitamin E. Further embodiments of the invention comprise, in addition to those ingredients as shown in Table 1, various amounts of carbohydrate, protein and fat, so that the weight percent of each component of the yeast fiber, carbohydrate, protein and fat can vary within a wide range. For example, a particular embodiment of the invention can comprise, in addition to those ingredients listed in Table 1, from about 0 grams to about 40 grams of protein per daily recommended intake of the supplement as in the third column of Table 1. Another embodiment of the invention can comprise, in addition to the ingredients in Table 1, from about 0 grams to about 60 grams of carbohydrate per daily recommended intake as in the third column of Table 1. A further embodiment can comprise, in addition to the ingredients in Table 1, from about 0 grams to about 50 grams of fat per daily recommended intake of the supplement as shown in Table 1.

The invention also pertains to a method for providing an individual with dietary supplementation that 1.) improves the serum lipid profile, 2.) lowers serum homocysteine, and 3.) provides an anti-oxidant to protect low density lipoproteins from oxidation, by administering to the individual a dietary supplement comprising yeast-derived fiber, folic acid, vitamin $B_6$, vitamin $B_{12}$, and vitamin E. The method can be carried out by administering to the individual any of the embodiments of the dietary supplements described herein, in effective doses and for sufficient treatment time.

The invention provides a dietary supplement which is effective in improving the serum lipid profile of an individual who consumes recommended amounts. Elevated levels of homocysteine in the blood are associated with increased risk of heart attack. By including folate and vitamin $B_6$, the dietary supplement provides the additional benefit of suppressing the level of homocysteine in the blood. A third benefit is provided by the anti-oxidant properties of vitamin E, particularly the effect of preserving low density lipoproteins from oxidation. The dietary supplement thus provides three mechanisms for improving the cardiovascular health of an individual. The method for improving serum cholesterol, and thereby reducing the risk of cardiovascular disease, can be more appealing to the individual than presently available methods of lowering cholesterol, such as cholesterol-lowering pharmaceuticals or ingestion of large amounts of oat fiber or psyllium.

DETAILED DESCRIPTION OF THE INVENTION

Figure 1:
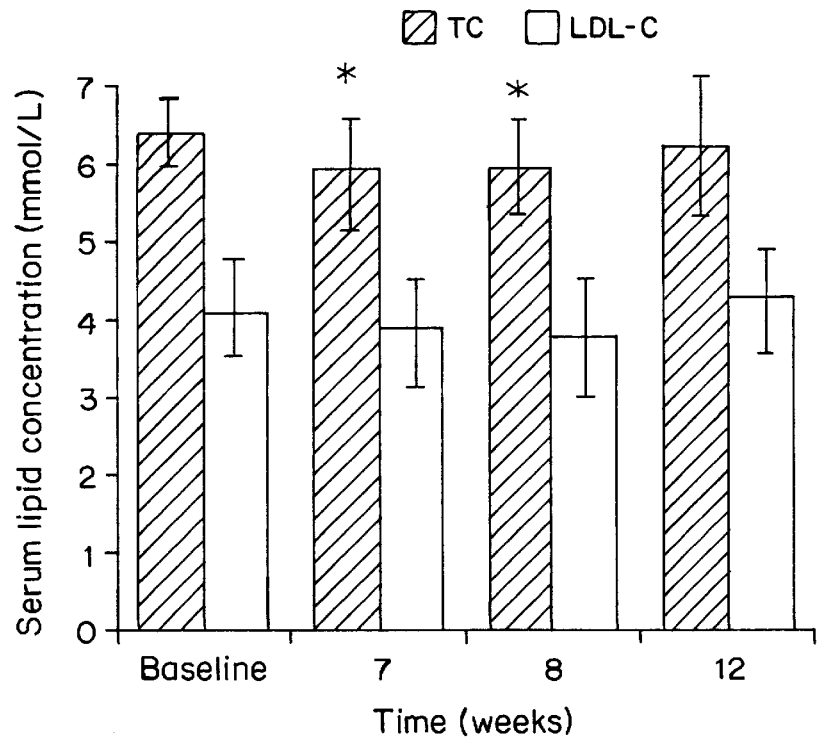
FIG. 1 is a graph showing changes in serum total cholesterol (TC; black bars) and low-density lipoprotein-cholesterol (LDL-C; open bars) concentrations (mmol/L) during yeast-derived β-glucan fiber supplementation (weeks 7 and 8) and during no supplementation (weeks 8 to 12) (n-15). Significant reductions were observed in concentrations of TC ($p<0.05$) and LDL-C ($p<0.001$) by one-way ANOVA with repeated measures. Significant reductions in TC (*$p<0.05$) were observed at week 7 and at week 8 compared to baseline by Bonferroni correction.

The invention relates to a dietary supplement comprising ingredients formulated to supply to a person an amount of yeast fiber required to achieve an improvement in the profile of serum cholesterol levels. Improving the serum cholesterol levels of a human includes one or more of the following: 1) an increase in HDL-C level; 2) a decrease in LDL-C level; and 3) a decrease in total cholesterol. Although other forms of fiber are known to have a beneficial effect on serum cholesterol levels, fiber derived from yeast (yeast fiber, and more specifically yeast β-glucan or yeast glucan-mannan as described in WO 97/02356, or glucomannan) has advantages over other forms of fiber, for example those from oats and psyllium, as described below. In addition, the dietary supplement of the invention supplies other vitamins beneficial to health that are likely to be in short supply in the diet of a person prone to heart disease, who in some cases has contributed to the disease by a diet high in animal fat and low in whole grain products, fruits and vegetables that supply the non-fiber ingredients of Table 1. Specifically, these vitamins are folic acid and vitamin $B_6$, vitamin $B_{12}$, including cyanocobalamin and other suitable forms of cobalamin, and vitamin E, as listed in Table 1.

TABLE 1

INGREDIENTS IN NUTRITIONAL SUPPLEMENT

| Nutrients | Optimal Recipe | Daily Intake (preferred range) |
| --- | --- | --- |
| Yeast-derived fiber | 15 g | 1–50 g (5–20 g) |
| Folic acid | 696 μg | 1–1,000 μg (180–800 μg) |
| Vitamin $B_6$ | 4.6 mg | 1–100 mg (1.6–4.6 mg) |
| Vitamin $B_{12}$ | 2.0 μg | 1–2,000 μg (1.5–4.0 μg) |
| Vitamin E | 200 I.U. | 10–800 I.U. (135–150 I.U) |

Yeast-derived β-glucan

Purified β-glucan can be produced from baker's or brewer's yeast (*Saccharomyces cerevisiae*) in a process that is consistent with the Food and Drug Administration (FDA) requirements for food-grade products. One such β-glucan product has been described in U.S. Pat. Nos. 4,962,094, 4,810,646, 4,992,540, 5,037,972, 5,082,936, 5,028,703, 5,250,436 and 5,506,124, the contents of which are all hereby incorporated by reference in their entirety. The intracellular contents of the yeast are hydrolyzed, preserving the β-glucan portion of the cell walls as discrete, intact, porous, hollow microspheres of 3–5 μm in diameter. The final product is a β-glucan which consists of a β-(1→6)-branched-, β-(1→3)-linked linear glucose polysaccharide. Typically, branching occurs with β-(1→6) chains at a frequency of 5% for every 20 glucose molecules linked by β-(1→3) chains. The remaining 15% of the product is glycogen as β-(1→4) glucose, chitin as β-(1→4) N-acetyl glucosamin, and water. The β-glucan product comprises soluble fiber and insoluble fiber, which gives it a creamy, rather than gummy character.

Yeast-derived β-glucan is more palatable than the oat-bran-derived β-glucan, and unlike the latter, yeast β-glucan is tasteless, odorless, colorless, not water soluble, and therefore non-gelling, even upon heating and cooling. The product is heat-stable (121° C. for 30 minutes), pH-stable (between 2 and 12), and shear-stable, because most of the β-(1→3) linkages are insoluble, unlike the soluble β-(1→4) linkages found in oat-bran. This attribute is of particular importance because the yeast-derived product can readily mix with liquids without gelling or forming an unpalatable viscous mass. The yeast-derived product, when added to liquids, has a creamy mouth-feel, and is therefore suitable for use in such products as salad dressings, frozen desserts, sour cream, cheese spreads, and the like.

Suitable yeast fiber can also be obtained from other species of yeast, for example: *Saccharomyces delbrueckii, Saccharomyces rosei, Saccharomyces microellipsodes, Saccharomyces carlsbergensis, Schizosaccharomyces pombe, Kluyveromyces lactis, Kluyveromyces fragilis, Kluyveromyces polysporus, Candida albicans, Candida cloacae, Candida tropicalis, Candida utilis, Hansenula wingei, Hansenula arni, Hansenula henricii* and *Hansenula americana*. In addition, yeast β-glucan-mannan preparations, such as those described in WO 97/02356, may also suitable for incorporation into foods.

Studies have shown that the vitamins folic acid and vitamin $B_6$, taken in excess of the RDA (recommended daily allowance), reduce the risk for developing heart disease by reducing levels of homocysteine. The best results were associated with an intake of folic acid of 696 βg (RDA=200) and an intake of vitamin $B_6$ of 4.6 mg per day (RDA=2.0;

Rimm, E. B., et al, "Folate and Vitamin B$_6$ from Diet and Supplements in Relation to Risk of Coronary Heart Disease Among Women, *JAMA,* 279:359–364 (1998)). Reductions in homocysteine are desirable because they are associated with arterial occlusive disease. The greatest reductions in homocysteine (14%) and increases in plasma folic acid (106%) are seen with intakes of folic acid of 665 µg. (Malinow, M. R., et al., "Reduction of Plasma Homocysteine Levels by Breakfast Cereals Fortified with Folic Acid in Patients with Coronary Heart Disease," *N. Engl. J. Med.* 338:1009–1015 (1998)). Homocysteine concentrations were reduced by 30% in mildly hypercholesterolemic men using a B-complex regimen of 1 mg folic acid, 7.2 mg vitamin B$_6$, and 2.0 µg vitamin B$_{12}$ (Woodside, J. V. et al., "Effect of B-group Vitamins and Antioxidant Vitamins on Hyperhomocysteinemia: A Double-Blind, Randomized, Factorial-Design, Controlled Trial," *Am. J. Clin. Nutr.* 67:858–866 (1988)).

The dietary supplement can further comprise carbohydrate, simple, medium chain length, or polysaccharides, or a combination thereof. A simple sugar can be chosen for desirable organoleptic properties. Uncooked cornstarch is one example of a complex carbohydrate. If it is desired that it should maintain its high molecular weight structure, it should be included only in food formulations or portions thereof which are not cooked or heat processed since the heat will break down the complex carbohydrate into simple carbohydrates, wherein simple carbohydrates are mono- or disaccharides. The dietary supplement contains, in one embodiment, combinations of sources of carbohydrate of three levels of chain length (simple, medium and complex; e.g., sucrose, maltodextrins, and uncooked cornstarch).

Sources of protein to be incorporated into the nutritional supplement of the invention can be any suitable protein utilized in nutritional formulations and can include whey protein, whey protein concentrate, whey powder, egg, soy flour, soy milk soy protein, soy protein isolate, caseinate (e.g., sodium caseinate, sodium calcium caseinate, calcium caseinate, potassium caseinate), animal and vegetable protein and mixtures thereof. When choosing a protein source, the biological value of the protein should be considered first, with the highest biological values being found in caseinate, whey, lactalbumin, egg albumin and whole egg proteins. In a preferred embodiment, the protein is a combination of whey protein concentrate and calcium caseinate. These proteins have high biological value; that is, they have a high proportion of the essential amino acids. See *Modern Nutrition in Health and Disease,* eighth edition, Lea & Febiger, publishers, 1986, especially Volume 1, pages 30–32.

Further Ingredients

The dietary supplement can also contain other ingredients in addition to those listed in Table 1, such as one or a combination of other vitamins, minerals, antioxidants, fiber and other dietary supplements (e.g., protein, amino acids, choline, lecithin, omega-3 fatty acids). Selection of one or several of these ingredients is a matter of formulation, design, consumer preference and end-user. The amounts of these ingredients added to the dietary supplements of this invention are readily known to the skilled artisan. Guidance to such amounts can be provided by the U.S. RDA doses for children and adults. Further vitamins and minerals that can be added include, but are not limited to, calcium phosphate or acetate, tribasic; potassium phosphate, dibasic; magnesium sulfate or oxide; salt (sodium chloride); potassium chloride or acetate; ascorbic acid; ferric orthophosphate; niacinamide; zinc sulfate or oxide; calcium pantothenate; copper gluconate; riboflavin; beta-carotene; pyridoxine hydrochloride; thiamin mononitrate; folic acid; biotin; chromium chloride or picolonate; potassium iodide; sodium selenate; sodium molybdate; phylloquinone; vitamin D$_3$; cyanocobalamin; sodium selenite; copper sulfate; vitamin A; vitamin C; inositol; potassium iodide.

Flavors, coloring agents, spices, nuts and the like can be incorporated into the product. Flavorings can be in the form of flavored extracts, volatile oils, chocolate flavorings, peanut butter flavoring, cookie crumbs, crisp rice, vanilla or any commercially available flavoring. Examples of useful flavoring include but are not limited to pure anise extract, imitation banana extract, imitation cherry extract, chocolate extract, pure lemon extract, pure orange extract, pure peppermint extract, imitation pineapple extract, imitation rum extract, imitation strawberry extract, or pure vanilla extract; or volatile oils, such as balm oil, bay oil, bergamot oil, cedarwood oil, walnut oil, cherry oil, cinnamon oil, clove oil, or peppermint oil; peanut butter, chocolate flavoring, vanilla cookie crumb, butterscotch or toffee. In one embodiment, the dietary supplement contains cocoa or chocolate.

Emulsifiers may be added for stability of the final product. Examples of suitable emulsifiers include, but are not limited to, lecithin (e.g., from egg or soy), and/or mono- and di-glycerides. Other emulsifiers are readily apparent to the skilled artisan and selection of suitable emulsifier(s) will depend, in part, upon the formulation and final product.

Preservatives may also be added to the dietary supplement to extend product shelf life. Preferably, preservatives such as potassium sorbate, sodium sorbate, potassium benzoate, sodium benzoate or calcium disodium EDTA are used.

In addition to the carbohydrates described above, the nutritional supplement can contain natural or artificial (preferably low calorie) sweeteners, e.g., saccharides, cyclamates, aspartamine, aspartame, acesulfame K, and/or sorbitol. Such artificial sweeteners can be desirable if the dietary supplement is intended to be consumed by an overweight or obese individual, or an individual with type II diabetes who is prone to hyperglycemia.

The dietary supplement can be provided in a variety of forms, and by a variety of production methods. These forms can include beverages, baked goods, puddings, confections, snack foods, or frozen confections or novelties.

In a preferred embodiment, to manufacture a food bar, the liquid ingredients are cooked; the dry ingredients are added with the liquid ingredients in a mixer and mixed until the dough phase is reached; the dough is put into an extruder, and extruded; the extruded dough is cut into appropriate lengths; and the product is cooled. The bars may contain other nutrients and fillers to enhance taste, in addition to the ingredients specifically listed herein.

Servings of the dietary supplement may vary in size and are not limited to units supplying the sum of the weights of the ingredients for the recipe or the recommended daily intake of nutrients listed in the third column of Table 1. A dietary supplement which supplies, in a recommended daily intake, nutrients comprising those listed in Table 1, can be ingested in various amounts throughout a given day, and the term "dietary supplement" is not intended to be limited to a particular weight or dose of the dietary supplement. It is understood by those of skill in the art that other ingredients can be added to those listed in Table 1, for example, fillers, emulsifiers, preservatives, etc. for the processing or manufacture of a food product.

An effective daily dose of yeast fiber is not as high in calories as foods that must be consumed to ingest an effective daily dose of oat fiber. As yeast fiber can be added to a variety of foods (e.g., ice cream, cheese, spreads, soups, sauces, puddings, and salad dressings), consumers can take in the necessary amount of lipid-lowering β-glucan in foods typically eaten in a normal day. Since the β-glucan can also function as a fat substitute, there is a potential for fewer total calories to be consumed.

Further embodiments

Further embodiments of the invention are methods for providing a human individual with dietary supplementation that improves serum lipid profiles. That is, after a sufficient consumption of a dietary supplement for a sufficient amount of time, the individual can be determined to have one or more of the following, compared to baseline levels: (1) a lower level of total cholesterol; (2) a lower level of low density lipoprotein-cholesterol; (3) a higher level of high-density lipoprotein-cholesterol. A "lower level" or a "higher level" as used above can include "significantly different" by standard statistical methods of comparison, for example where $p<0.05$ by Student's t test, or by one-way ANOVA. As demonstrated in the Exemplification herein, the period of time necessary to observe one or more of these changes can be several weeks.

The methods of the invention can be carried out by administering the dietary supplement described herein, to be consumed orally in one or more daily doses, preferably by administering a number of small doses (one to four doses are preferred) throughout the day, the doses to add up each day to the daily intake of each ingredient, and more preferably, the preferred range of each ingredient, as listed in the third column of Table 1. The dietary supplement of the invention may be administered to an individual either alone or with other foods or beverages, as in a meal or snack.

The dietary supplement can be administered to an individual in the form of a powder, for instance to be used by mixing into a beverage, or by stirring into a semi-solid food such as a pudding, topping, sauce, puree, cooked cereal, or salad dressing, for instance, or by otherwise adding to a food. The dietary supplement can also be incorporated into baked goods such as breads, crackers, cookies, cakes, granola bars, rice cakes, croutons prepared cereals and the like, preferably having a low proportion of fat, such as 30% or less, and having artificial sweeteners, when appropriate, to limit the total number of calories. The dietary supplement can also be administered to the individual in the form of one or more tablets or capsules wherein the tablet or capsule comprises one or more inert ingredients, especially if it is desirable to limit the number of calories added to the diet by the dietary supplement.

The present invention is illustrated by the following examples, which are not intended to be limiting in any way. All references cited herein are hereby incorporated by reference in their entirety.

EXEMPLIFICATION

Subjects

Male subjects were selected from an obese population seen at the Beth Israel Deaconess Medical Center's Nutrition Research Clinic; others responded to local newspaper advertisements. At entry, subjects were between the ages of 20 and 60, were at least 120% of ideal weight, and had serum TC (total cholesterol as measured in serum) concentrations over 6.21 mmol/L (240 mg/dL). Candidates taking cholesterol-lowering medication or having secondary causes of hyperlipidemia such as hypothyroidism, diabetes mellitus, or renal disease were excluded from the study. The study protocol was approved by the Beth Israel Deaconess Medical Center Institutional Review Board.

Nineteen male subjects entered the study, but four of the 15 subjects dropped out during the 3-week wash-in period. A total of 15 subjects completed the study and had blood lipid data available for basal values, week 7, week 8 and week 12. Of the 15 subjects who completed the study, only 12 of them had data relating to anthropometry, nutrient intake and clinical tolerance.

Study Design and Measurements

Each subject had three fasting blood samples drawn weekly over 3 weeks for measurement of TC and triglycerides (TGs). These measurements were then averaged as the basal values for each patient. Both TC and high-density lipoprotein-cholesterol (HDL-C) were measured directly. The concentrations of LDL-C (mg/dL) were calculated according to the method of Friedewalt et al. (Friedewaldt, W. T., Levy R I, Fredrickson D S. Estimation of low density lipoprotein cholesterol concentration in plasma without the use of preparative ultracentrifuge. *Clin. Chem.*18:499–502 (1972)). LDL-C=TC-(HDL-C)-(triglycerides/5). Cholesterol was converted from mg/dL to mmol/L by multiplying by 0.02586. Plasma TGs were converted from mg/dL to mmol/L by multiplying by 0.0112. After the third blood sample, subjects were instructed how to take 15 g of the yeast-derived β-glucan fiber in pre-weighed containers of 7.5 g and add it to orange juice twice a day. Subjects returned weekly for 8 weeks to be weighed and to obtain more fiber. They were not instructed to follow a special diet. Subjects completed weekly 3-day food records during the baseline (3 weeks) and treatment periods (8 weeks). Fiber intake was confirmed by the number of empty containers returned. At week 7 and 8, 12-hour fasting levels of plasma TC, HDL-C, LDL-C, and TGs were measured. Fiber supplementation stopped after 8 weeks, but the subjects continued consuming the same amount of orange juice. Four weeks later (week 12), the subjects were weighed and had another fasting blood sample taken for TC, LDL-C, HDL-C, and TGs measurements.

Each week the fiber was consumed, subjects completed questionnaires designed to gauge the effect of the product. Assessment was made of (1) the degree of satiety (when the subject felt fullness, general feeling of fullness throughout the day), (2) product tolerance (abdominal discomfort, diarrhea, nausea, vomiting, and flatulence), and (3) product acceptability (thickness, consistency, color, flavor, aroma, and aftertaste). Satiety was rated on a scale of 0 to 10, with 0 being "hungry" and 10 being "extremely full." Tolerance was assessed at four levels: 0 for no adverse effects, 1 for slight awareness, 2 for moderate discomfort, and 3 for marked discomfort. Product acceptability was rated on a scale of I to 9, with one being the worst attribute (e.g., gritty-chalky consistency) and 9 the best attribute (e.g., smooth consistency).

Statistical Analysis

Data were presented as means±standard deviation (SD), except for satiety, tolerance, and acceptability, which were presented as means and medians. One-way ANOVA was used for univariate and multivariate repeated measures analysis (more than one measurement on each subject) using SYSTAT statistical software program (SYSTAT, Evanston, Ill.). The significance was determined at the 95% confidence level. Group comparison between the baseline value and each of the treatment (week 7, week 8 and post-treatment [week 12]) weeks was determined by Bonferroni corrections, only when ANOVA, as defined above, was found to be significant.

RESULTS

Fifteen male subjects completed the study; four subjects dropped out during the 3-week wash-in period. Subjects were middle-aged (51±7 years) and were overweight in terms of BMI (27.7±5 kg/m$^2$) (Table 2). Nutrient intake during the baseline and fiber-treatment periods was similar (9.23±2.16 MJ baseline versus 11.61±1.61 MJ during treatment) except for the fiber supplement during the treatment phase. All subjects consumed 15 g of fiber daily in addition to their usual diet during the 8-week study period. Subjects consumed sufficient energy to maintain their body weight during the study.

Changes in Plasma Lipids

Figure 2:
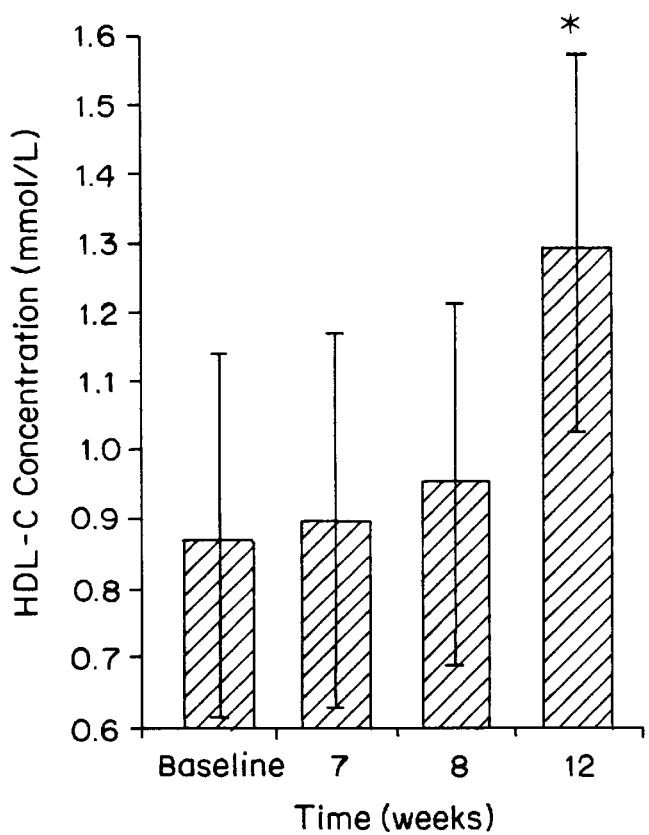
FIG. 2 is a graph showing changes in serum high-density lipoprotein-cholesterol (HDL-C) concentrations (mmol/L) during yeast-derived β-glucan fiber supplementation (weeks 7 and 8) and during no supplementation (weeks 8 to 12) (n-15). A significant reduction was observed in the concentration of HDL-C ($p<0.005$) by one-way ANOVA with repeated measures. The concentration of HDL-C increased from baseline to week 7 and to week 8, but did not achieve significance because repeated paired values were compared. For HDL-C, a significant group difference (*$p<0.05$) was observed between baseline and week 12 by the Bonferroni correction.

Significant differences were found in TC concentrations ($p<0.05$), LDL-C ($p<0.001$), and HDL-C ($p<0.005$) by one-way ANOVA with repeated measures (FIG. 1 and FIG. 2). After 7 weeks of fiber supplementation, serum TC was significantly lower (8%) than baseline (6.38+0.44 mmol/L versus 5.90±0.68 mmol/L) ($p<0.05$ by Bonferroni correction). At week 8, TC was 5.98±0.57 mmol/L, which was also significantly lower (6%) than baseline ($p<0.01$ by Bonferroni correction). There was no difference in TC between baseline and week 12.

During the study period, the levels of HDL-C were significantly increased ($p<0.005$ by one-way ANOVA). The mean concentration increased (9%) from 0.87±0.25 mmol/L at the basal period to 0.96±0.26 mmol/L at week 8 (FIG. 2). However, a group difference was only observed between basal and week 12 ($p<0.05$ with Bonferroni correction), indicating a carryover effect even though the fiber supplementation had stopped 4 weeks earlier. There was a 16% increase in HDL-C at week 12 compared to baseline values.

For LDL-C concentration, no significant differences were observed between basal values and weeks 7, 8, and 12 when comparing individual groups using Bonferroni correction even though the overall ANOVA with repeated measures was highly significant ($p<0.001$). Compared to baseline values, LDL-C declined 5% at week 7 and 8% at week 8.

Figure 3:
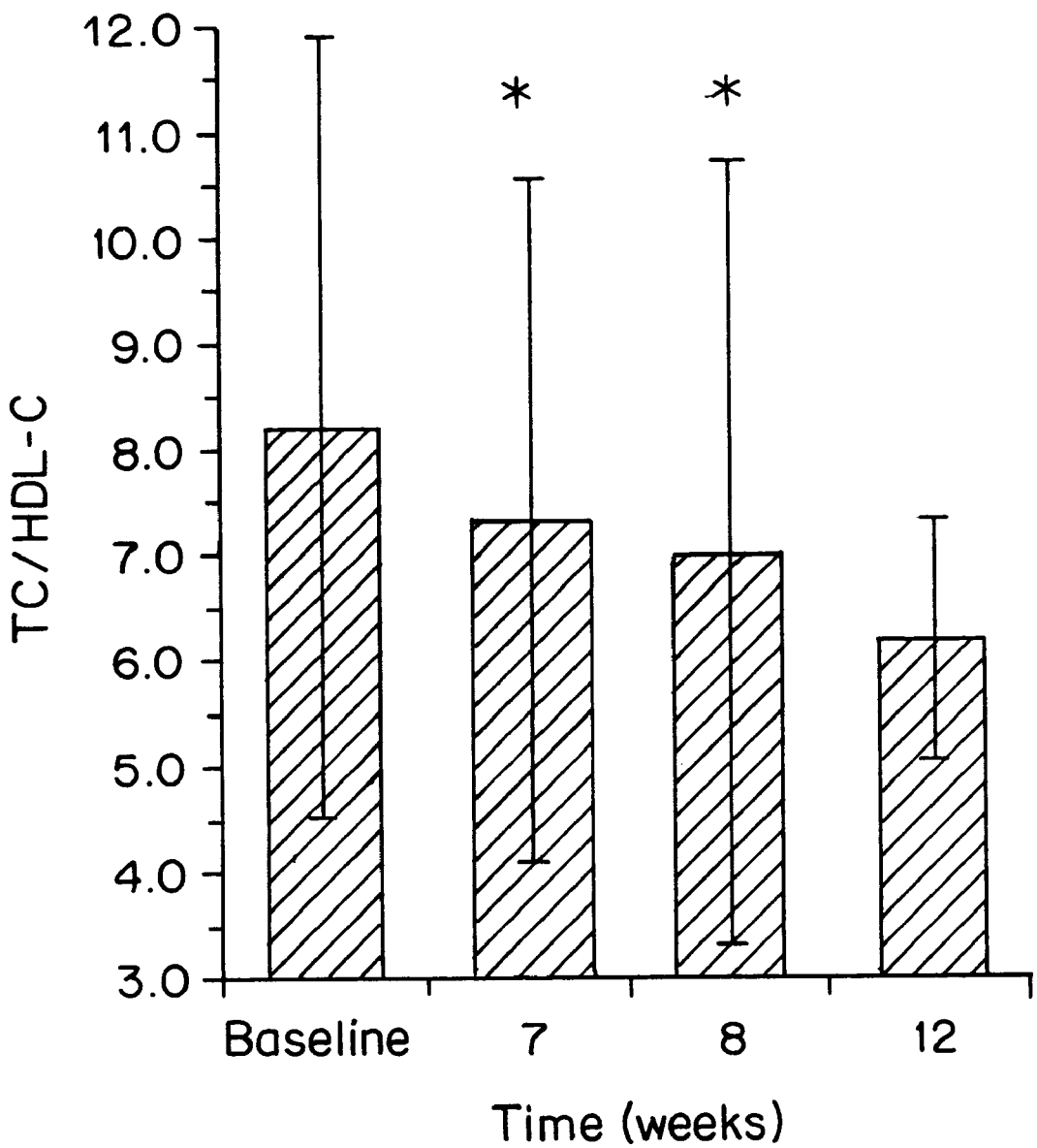
FIG. 3 is a graph showing changes in the ratio of total cholesterol (TC) to high-density lipoprotein-cholesterol (HDL-C) concentrations (mmol/L) during yeast-derived β-glucan fiber supplementation (weeks 7 and 8) and during no supplementation (weeks 8 to 12) (n-15). Borderline overall significant decreases (p-0.06) were observed in the ratio with one-way ANOVA with repeated measures analysis. The overall decrease was significant by the single degree-of-freedom polynomial contrast ($p<0.05$) as were individual comparisons between baseline and week 7 and baseline and week 8 (*$<0.05$) by the Bonferroni correction.

The mean ratio to TC/HDL-C declined during fiber supplementation, which was marginally significant ($p<0.06$) by one-way ANOVA with repeated measures analysis (FIG. 3). However, this ratio was significant ($p<0.05$) by the single degree-of-freedom polynomial contrast. Fiber supplementation led to a reduction in the ratio of TC/HDL-C from 8.2 to 7.3 at week 7 ($p<0.005$ with Bonferroni correction) and to 7.0 at week 8 ($p<0.05$ with Bonferroni correction). This ratio returned to basal value at week 12.

Satiety, Tolerance, Acceptability

Data were available for 12 for the 15 subjects. Six subjects stated that they never felt full after taking the fiber supplement; five felt full 5 to 20 minutes after ingestion. The remainder felt full from 20 to 60 minutes after ingestion. Most subjects (8/14) stated that beyond 3 hours after ingestion of the fiber they had no feeling of fullness. When subjects rated fullness on a scale of 1 to 10, mean fullness ranged from 2.8 out of 10, three hours after ingestion of the fiber, to 3.9 out of 10, one hour after ingestion (Table 3).

The effect of the fiber on diarrhea, nausea, abdominal discomfort, abdominal distension and flatulence (Table 3) was minimal (less than 1, indicating slight awareness of symptoms easily tolerated). There were no reports of vomiting.

The product was moderately well accepted (Table 3). Each of the six attributes rated (thickness, consistency, color, flavor, aroma, and aftertaste) had a mean and median of 4 or 5 on a scale of 0 to 9.

TABLE 2

Nutrient Intakes,[1] Weight, and BMI Before and After Yeast-Fiber Supplementation

| Nutrient/Weight | Average Baseline Data (3-week wash-in period) | Average Treatment Data (after 8 weeks of fiber) |
| --- | --- | --- |
| Energy (kJ) | 9,227 ± 2,155[2] | 11,605 ± 1,609 |
| Dietary fiber (g) | 17 ± 3 | 19 ± 4 (plus 15 g of yeast β-glucan) |
| Fat (% of total energy) | 32 ± 6 | 31 ± 6 |
| Saturated fat (% of total energy) | 11 ± 2 | 11 ± 3 |
| Monounsaturated fat (% of total energy) | 12 ± 3 | 12 ± 2 |
| Polyunsaturated fat (% of total energy) | 6 ± 1 | 7 ± 1 |
| Cholesterol (mg) | 302 ± 122 | 346 ± 95 |
| Weight (kg) | 99 ± 9 | 98 ± 9 |
| BMI (kg/m$^2$) | 27.7 ± 5 | 27.5 ± 5 |

[1]Data available for 12 subjects
[2]Mean ± S.D.

TABLE 3

Satiety/Tolerance/Acceptability During Ingestion of Fiber[1]

| Satiety | Tolerance | Acceptability |
| --- | --- | --- |
| Fullness 1 hour after fiber use: 3.9/4[2] | Diarrhea: 0.14/0[3] | Thickness (1 = too thin to 9 = too thick): 5.2/5[4] |
| Fullness 2 hours after fiber use: 3.4/4 | Nausea: 0.09/0 | Consistency (1 = gritty/chalky to 9 = smooth): 4.8/5 |
| Fullness 3 hours after fiber use: 2.8/4 | Vomiting: 0/0 | Color (1 = unappealing to 9 = appealing): 4.4/4 |
| Fullness during the day after fiber use: 3.3/4 | Abdominal discomfort: 0.19/0 | Flavor (1 = unpleasant to 9 = pleasant): 4.6/5 |
| | Abdominal distension: 0.15/0 | Aroma (1 = unpleasant to 9 = pleasant): 4.9/5 |
| | Flatulence: 0.37/0 | Aftertaste (1 = nauseating to 9 = delicious): 4.9.5 |

[1]Data available for 12 subjects
[2]Mean/median based on a satiety scale from 0 (hungry) to 10 (extremely full)
[3]Mean/median based on a scale of severity from 0 (no adverse effects) to 3 (marked discomfort, unable to perform usual daily activity)
[4]Mean/median based on an acceptance scale of 1 to 9

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A dietary supplement comprising about 1 gram to about 50 grams yeast-derived fiber, about 1 μg to about 1,000 μg folic acid, about 1 mg to about 100 mg vitamin B$_6$, about 1 μg to about 2,000 μg vitamin B$_{12}$, and about 10 I.U. to about 800 I.U. vitamin E; wherein the yeast-derived fiber is glucomannan.

2. A dietary supplement comprising about 1 gram to about 50 grams yeast-derived fiber, about 1 μg to about 1,000 μg folic acid, about 1 mg to about 100 mg vitamin B$_6$, about 1 μg to about 2,000 μg vitamin B$_{12}$, and about 10 I.U. to about 800 I.U. vitamin E; wherein the yeast-derived fiber comprises β-glucan and glucomannan.

3. A dietary supplement which supplies, in a recommended daily intake of the dietary supplement, nutrients comprising from about 1 gram to about 50 grams yeast-derived fiber, from about 1 μg to about 1,000 μg folic acid, from about 1 mg to about 100 mg vitamin $B_6$, from about 1 μg to about 2,000 μg vitamin $B_{12}$, and from about 10 I.U. to about 800 I.U. vitamin E; wherein the dietary supplement is in the form of a food bar.

4. The dietary supplement of claim 3, wherein the yeast-derived fiber is β-glucan.

5. The dietary supplement of claim 3, wherein the yeast-derived fiber is obtained from *Saccharomyces cerevisiae*.

6. The dietary supplement of claim 3 which further supplies, in a recommended daily intake of the dietary supplement, nutrients comprising up to about 60 grams carbohydrate.

7. The dietary supplement of claim 3 which further supplies, in a recommended daily intake of the dietary supplement, nutrients comprising up to about 40 grams protein.

8. The dietary supplement of claim 3 which further supplies, in a recommended daily intake of the dietary supplement, nutrients comprising up to about 50 grams fat.

9. The dietary supplement of claim 3 which further comprises one or more sweeteners.

10. A method for providing an individual with dietary supplementation that improves serum lipids, comprising administering to an individual in need of dietary supplementation that improves serum lipids the dietary supplement of claim 3.

11. A method for providing a source of dietary fiber, comprising administering to an individual in need of a source of dietary fiber the dietary supplement of claim 3.

12. A method for improving the cardiovascular health of an individual, comprising administering to an individual in need of improvement of cardiovascular health the dietary supplement of claim 3.

13. A dietary supplement which supplies, in a recommended daily intake of the dietary supplement, nutrients comprising from about 5 grams to about 20 grams yeast-derived fiber, from about 180 μg to about 800 μg folic acid, from about 1.6 mg to about 4.6 mg vitamin $B_6$, from about 1.5 μg to about 4 μg vitamin $B_{12}$, and from about 135 I.U. to about 150 I.U. vitamin E; wherein the dietary supplement is in the form of a food bar.

14. A method for providing an individual with dietary supplementation that improves serum cholesterol levels, comprising administering to an individual in need of dietary supplementation that improves serum cholesterol levels the dietary supplement of claim 13.

15. A method for providing a source of dietary fiber, comprising administering to an individual in need of a source of dietary fiber the dietary supplement of claim 13.

16. A method for improving the cardiovascular health of an individual, comprising administering to an individual in need of improvement of cardiovascular health the dietary supplement of claim 13.

17. A method for providing an individual with dietary supplementation that improves serum cholesterol levels, comprising administering to an individual in need of dietary supplementation that improves serum cholesterol levels a dietary supplement, comprising yeast-derived fiber, folic acid, vitamin $B_6$, vitamin $B_{12}$, and vitamin E; wherein the dietary supplement is in the form of a food bar.

* * * * *